(12) United States Patent
LeJeune et al.

(10) Patent No.: US 6,750,033 B2
(45) Date of Patent: Jun. 15, 2004

(54) POSITIVE RESPONSE BIOSENSORS AND OTHER SENSORS

(75) Inventors: Keith E. LeJeune, Pittsburgh, PA (US); Markus Erbeldinger, Pittsburgh, PA (US)

(73) Assignee: Agentase, LLC, Pittsburgh, PA (US)

( * ) Notice: Subject to any disclaimer, the term of this patent is extended or adjusted under 35 U.S.C. 154(b) by 0 days.

(21) Appl. No.: 09/850,686

(22) Filed: May 7, 2001

(65) Prior Publication Data

US 2002/0182662 A1 Dec. 5, 2002

(51) Int. Cl.⁷ .............................. C12Q 1/34; C12Q 1/00; C12Q 1/44

(52) U.S. Cl. ............................... 435/18; 435/4; 435/19; 435/183; 435/283.1; 435/287.1; 435/963; 435/7.1

(58) Field of Search ............................... 435/18, 4, 19, 435/183, 283.1, 287.1, 963, 7.1

(56) References Cited

U.S. PATENT DOCUMENTS

| | | | |
|---|---|---|---|
| 3,791,927 A | 7/1971 | Forgione | 195/63 |
| 4,324,858 A | 6/1980 | Goodson | 435/20 |
| 4,525,704 A | 11/1983 | Campbell | 340/632 |
| 5,272,061 A | 9/1991 | Hasselberg | 435/20 |
| 6,001,556 A | 1/1996 | Charych | 435/5 |
| 5,496,701 A * | 3/1996 | Pollard-Knight | 435/7.4 |
| 5,858,186 A | 12/1996 | Glass | 204/403 |
| 5,945,343 A | 8/1997 | Munkholm | 436/108 |
| 5,958,786 A | 8/1997 | Munkholm | 436/98 |
| 5,919,576 A | 11/1997 | Hui | 428/545 |
| 6,291,200 B1 * | 9/2001 | LeJeune et al. | 435/20 |

FOREIGN PATENT DOCUMENTS

| | | |
|---|---|---|
| WO | WO 02/090577 | 11/2002 |

OTHER PUBLICATIONS

Rogers, K.R., Biosensors Bioelectronics, 10,533 (1995).
Parente, A.H., Marques, E. T. Jr., Appl. Biochem. Biotechnol. 37, 3, 267 (1992).
Yang, S., Atanasov, P., Wilkins, E., Ann. Biomed. Eng., 23, 6, 833 (1995).
Turner, A. P. F., Sensors Actuators, 17, 433 (1989).
Evtugyn, G. A., Budnikov, H. C., Kolskaya, Talanta, 46, 465 (1998).
Copy of Communication from the European Patent Office enclosing Supplementary European Seach Report corresponding to a related case (i.e., the parent case) (Jan. 23, 2003).

(List continued on next page.)

*Primary Examiner*—Louise N. Leary
(74) *Attorney, Agent, or Firm*—Buchanan Ingersoll PC; Craig G. Cochenour (57) ABSTRACT

A sensor for detecting an analyte in an environment includes a first reaction system including a first enzyme and a substrate for the first enzyme. The analyte inhibits the reaction of the substrate catalyzed by the first enzyme (in other words, the analyte inhibits the first enzyme). The sensor further includes at least a second reaction system that reacts to produce a first detectable state when the first enzyme is inhibited. In some embodiments, the reaction of the first reaction system can produce a second detectible state, different from the first detectible state. Another sensor for detecting an analyte in an environment includes a first reaction system including a first enzyme or a first substrate for the first enzyme. In this embodiment, the analyte is either a substrate for the first enzyme if the first reaction system includes the first enzyme or the first enzyme if the first reaction system includes the first substrate. The sensor also includes at least a second reaction system that reacts to produce a first detectable state when the analyte is below a certain concentration. The sensor thus provides a positive or detectible response when the analyte is absent or deficient. Once again, the first reaction can produce a second detectible state, different from the first detectible state.

54 Claims, 6 Drawing Sheets butyrylcholinesterase hydrolyses butyrylcholine + H₂0 ⟶ butyric acid + choline    ↓ pH down urease hydrolyses urea + 2 H₂0 ⟶ 2 ammonia + carbon dioxide    ↑ pH up

OTHER PUBLICATIONS

Otto S. Wolfbeis et al. "Recent Progress in Optical Oxygen Sensing". Optical Fibers in Medicine III, Los Angeles, CA, 13–16 Jan. 1988, vol. 906, 42–48.

Alumni Newsletter, University of Pittsburgh, Department of Chemical and Petroleum Engineering, Online 1999.

Young Ae Cho et al. "Fabrication of Butyrylcholineesterase Sensor Using Polyurethane–Based Ion–Selective Membranes". Biosensors & Bioelectronics. England Apr. 30, 1999. vol. 14, No. 4 Apr. 30, 1999.

Jaroslav Katrlik et al. "Composite Alcohol Biosensors Based On Solid Binding Matrix". Biosensors & Bioelectronics, Feb. 1, 1998. Elsevier, UK, vol. 13, no. 2, 181–191.

* cited by examiner

POSITIVE RESPONSE BIOSENSORS AND OTHER SENSORS

BACKGROUND OF THE INVENTION

The present invention relates to positive response sensors and, particularly, to enzymatic biosensors in which two reaction schemes provide a positive response.

There are many types of sensors designed to detect the presence of chemical species, for example, on surfaces or within solutions. Such sensors exhibit signals based on a wide variety of chemical, electrical, or physical responses. Many such sensors are based upon "negative responses". In negative response sensors, the chemical analyte of interest inhibits or retards a chemical or physical process that would otherwise take place within the sensor in the analyte's absence. The term "negative response sensor" thus generally refers sensors in which the presence of a target analyte results in the absence of or the reduction of a signal change or a signal change.

Enzymatic proteins are remarkable natural catalysts in that they selectively catalyze many reactions under relatively mild reaction conditions. Enzymes also offer the potential to perform sterio- and regio-selective reactions not readily accomplished with conventional chemistry. As used herein, the term "enzyme" refers generally to proteins that catalyze biochemical reactions. These "biopolymers" include amide-linked amino acids and typically have molecular weights of 5,000 or greater. A compound for which a particular enzyme catalyzes a reaction is typically referred to as a "substrate" of the enzyme.

In general, six classes or types of enzymes (as classified by the type of reaction that is catalyzed) are recognized. Enzymes catalyzing reduction/oxidation or redox reactions are referred to generally as EC 1 (Enzyme Class 1) Oxidoreductases. Enzymes catalyzing the transfer of specific radicals or groups are referred to generally as EC 2 Transferases. Enzymes catalyzing hydrolysis are referred to generally as EC 3 hydrolases. Enzymes catalyzing removal from or addition to a substrate of specific chemical groups are referred to generally as EC 4 Lyases. Enzymes catalyzing isomeration are referred to generally as EC 5 Isomerases. Enzymes catalyzing combination or binding together of substrate units are referred to generally as EC 6 Ligases.

Enzymes have been known since the early 1960's to be useful tools for detecting the presence of chemical species. Rogers, K. R., Biosensors Bioelectronics, 10, 533 (1995). A number of enzymatic biosensors have been designed to detect a variety of different compounds including, for example, glucose, creatinine, urea, and cholinesterase inhibitors. Parente, A. H., Marques, E. T. Jr., *Appl. Biochem. Biotechnol.* 37, 3, 267 (1992); Yang, S., Atanasov, P., Wilkins, E., *Ann. Biomed. Eng.*, 23, 6, 833 (1995). U.S. Pat. No. 5,858,186 describes a urea-based biosensor in which substrate hydrolysis is monitored with a pH electrode. U.S. Pat. Nos. 5,945,343 and 5,958,786 describe enzyme-based polymer sensors which fluoresce in the presence of ammonia, which is enzymatically produced from urea and creatinine respectively. In addition U.S. Pat. No. 4,324,858 describes the utilization of cholinesterase for the colorimetric detection of organophosphorus pesticides and nerve agents. A related patent, U.S. Pat. No. 4,525,704 describes the use of cholinesterases and electrical currents in detecting toxic gases.

Generally, enzymatic biosensors function by one of two methods: (1) the sensing enzyme converts an otherwise undetectable compound into another or series of compounds which can be detected by visual, chemical, or electrical techniques; or (2) the enzyme is inhibited by the presence of the compound of interest and enzyme inhibition is linked to a measurable quantity.

Independent of the method of use, the signals of enzyme-based biosensors are often limited in practical application by the nature of enzyme activity. Only in the case of enzyme substrate detection does the sensor provide a positive response in the presence of target analyte. In other words a noticeable change in the sensor indicates the presence of a target analyte. If the detection of enzyme inhibitors or the detection of substrate deficiency is desired, existing approaches rely on negative response signals, or the absence or reduction of an enzymatic reaction, to indicate the presence of inhibitors or the absence of target compounds.

For example, many commercially available nerve agent sensors are based on the inhibition of cholinesterases. The presence of nerve agents blocks the catalytic side on cholinesterase, disabling its ability to catalyze reactions. Such a sensor is employed by exposing the sensing enzyme (cholinesterase) to a questionable environment. Cholinesterase substrate is later applied. Depending upon the substrate or assay system employed, cholinesterase activity may result in a pH change, color change or fluorescent signal. In each of these negative response systems, a signal change occurs only in the absence of analyte (nerve agents). The initial signal of the sensor is unchanged in the presence of analyte. Kumaran, S., and Morita, M. *Talanta*, 42, 649 (1995). Campanella, L., Colapicchioni, C., Favero, G., Sammartino, M. P. and Tomassetti, M. *Sensors and Actuators B*, 33, 25 (1996). Hart, A. L., Collier, W. A., and Janssen, D. *Biosensors & Bioelectronics*, 12, 545–654 (1997). Cho, Y. A., Lee, H. S., Cha, G. S., and Lee, Y. T. *Biosensors & Bioelectronics*, 14, 387–390 (1999). Bachmann, T. T., and Schmidt, R. D. Analytica Chimica Acta, 401, 95 (1999). Diaz, A., and Ramos Peinado, M. C. *Sensors and Actuators B*, 38–39, 426 (1997).

It is very desirable to develop sensors and sensing method through which the non-intuitive nature of negative response sensors can be changed to a more intuitive positive response system.

SUMMARY OF THE INVENTION

In general, the present invention provides sensors and methods in which the non-intuitive nature of a previously negative response sensor is changed to a more intuitive, positive response system. The present invention is well suited for application in enzymatic biosensors and enzymatic biosensing methods.

In one aspect, the present invention provides a sensor for detecting an analyte in an environment including a first reaction system including at least a first enzyme and at least one substrate for the first enzyme. The analyte inhibits the reaction of the substrate catalyzed by the first enzyme (in other words, the analyte inhibits the first enzyme). The sensor further includes at least a second reaction system that reacts to produce a first detectable state when the first enzyme is inhibited. In some embodiments, the reaction of the first reaction system can produce a second detectible state, different from the first detectible state.

In one embodiment, the reaction of the first reaction system (that is, the reaction of the substrate catalyzed by the first enzyme) causes pH to change in a first direction, and the reaction of the second reaction system causes pH to change in a second direction, opposite of the first direction. The first enzyme can, for example, be a hydrolase, which catalyze hydrolysis reactions, typically resulting in a pH change.

The second reaction system can, for example, include a second enzyme and a substrate for the second enzyme. The second reaction system can also involve a non-enzymatic, chemical reaction. In the case that the second reaction system includes a second enzyme, the first enzyme can, for example, be a hydrolase and the second enzyme can, for example, be a different hydrolase.

The first enzyme and/or the second enzyme can, for example, be immobilized in a polymer medium (for example, in a sponge-like polyurethane) or be in solution. Substrates can, for example, be added to the polymer medium in solution or as a powder.

The first detectible state can, for example, be a colorimetric change. As used herein, the phrase "colorimetric change" refers generally to a detectible change in color. The colorimetric change can be detectible with the human eye or with instrumentation as known in the art.

As set forth above, the reaction of the first reaction system can produce a second detectible state that is different from the first detectible state. For example, the first detectible state can arise from the presence of a first pH sensitive dye producing a colorimetric change, and the second detectible state can be a colorimetric change different from the colorimetric change of the first detectible state.

In another embodiment, the reaction of the first reaction system causes a first colorimetric change and the reaction of the second reaction system causes a second colorimetric change. The second colorimetric change is different from the first colorimetric change.

Furthermore, the reaction of the first reaction system can, for example, cause pH to change in a first direction and the reaction of the second reaction system can cause a pH sensitive colorimetric change when the first enzyme is inhibited.

In another aspect, the present invention provides a sensor for detecting an analyte in an environment including a first reaction system including at least a first enzyme or at least one substrate of the first enzyme. In this embodiment, the analyte is a substrate for the first enzyme if the first reaction system includes the first enzyme, or the analyte is the first enzyme if the first reaction system includes a substrate of the first enzyme. The sensor also includes at least a second reaction system that reacts to produce a first detectable state when the analyte is below a certain concentration. The sensor thus provides a positive or detectible response when the analyte is absent or deficient. Once again, the enzymatically catalyzed reaction of the first reaction system can produce a second detectible state, different from the first detectible state.

In one embodiment, the reaction catalyzed by the first enzyme causes pH to change in a first direction and the reaction of the second reaction system causes pH to change in a second direction, opposite of the first direction.

In another embodiment, the first detectible state arises from the presence of a first pH sensitive dye producing a colorimetric change, and the second detectible state is a colorimetric change different from the colorimetric change of the first detectible state.

In still another embodiment, the reaction of the first reaction system causes pH to change in a first direction and the reaction of the second reaction system causes a pH sensitive colorimetric change when the analyte is below a certain concentration.

The present invention also provides a method of detecting an analyte in an environment including the steps of: providing a first reaction system including a first enzyme and a substrate for the first enzyme, the analyte inhibiting the first enzyme; and providing at least a second reaction system that reacts to produce a first detectable state when the first enzyme is inhibited.

In another aspect, the present invention provides a method for detecting an analyte in an environment including the step of: providing a first reaction system including a first enzyme or a substrate of the first enzyme. The analyte is a substrate for the first enzyme if the first reaction system includes the first enzyme. The analyte is the first enzyme if the first reaction system includes a substrate of the first enzyme. The method also includes the step of providing at least a second reaction system that reacts to produce a first detectable state when the analyte is below a certain concentration.

The present invention thus provides sensors and methods to detect the presence of an enzyme inhibitor or a substrate deficiency (or absence) with a positive signal in form of, for example, changing pH or changing color. Change of pH can be visualized by utilizing pH dyes, electrical equipment, electrodes, or special devices. Once again, color changes can be either inside or outside the visible range, detectable by naked eye or optical instruments. The present invention provides sensors for and methods of monitoring the absence of an enzymatic reaction as a result of inhibitor presence or substrate deficiency (or absence) by, for example, combining a sensing enzyme with the use of an additional enzyme/substrate pair or an additional colorimetric chemical reaction.

The sensors and methods of the present invention can be employed with a wide range of sensing enzymes. As discussed above, several preferred embodiments include hydrolase enzymes such as, for example, lipases, phosphatases, amylases, cellulases, proteases, peptidases, ureases, and deaminases. In general, while catalyzing substrate hydrolysis, each of these hydrolase enzymes causes a corresponding signal, which can, for example, be changing pH, the formation of colorimetric products, or a combination of both. In several embodiments, the sensing enzyme(s) are paired with a second enzyme-substrate combination or a colorimetric chemical reaction. The choice of a second reaction can, for example, depend on the hydrolysis product(s) of the first enzyme in the case of a hydrolase. For example, to compensate the production of hydroxyl or hydronium ions by the first or sensing enzyme, the second reaction can yield hydronium or hydroxyl ions, respectively. In the absence of first enzyme activity, the second reaction produces an excess of either hydroxyl or hydronium ions resulting in a detectible change of pH.

The first or sensing enzyme is not limited to hydrolases, however. In that regard, other classes of enzymes including, but not limited to, oxidoreductases and transferases are suitable using, for example, the formation of colorimetric products. For example, the enzyme peroxidase in combination with the colorimetric substrate dianisidine is suitable to indicate the presence of peroxide.

To compensate the production of colorimetric products by the sensing enzyme, a second reaction can, for example yield a different color capable of changing the overall sensor signal to a third color. In the absence of sensing enzyme activity, the sensor signal indicates the color of this second reaction. For example if a sensing enzyme reaction results in a blue product, a second reaction that yields a yellow product can be used. Both reactions combined yield a green color, whereas the sensor produces only yellow color in the absence of sensing enzyme activity.

While the utilization of enzymes in sensing applications has become commonplace, the sensors and methods of the present invention dramatically improve the signal of such biosensors. There are countless imaginable sensing applications wherein the sensor analyte generates no or reduced enzyme activity. In applications such as sensing of enzyme inhibitors or the deficiency of target compounds, a signal is commonly not achievable with the existing biosensor technology. By definition there is either no or reduced enzyme activity in the presence of inhibitors or the deficiency of the target compound. Turning such negative responses into a much more informative and intuitive positive response is a substantial improvement in the art.

Although the sensors and methods of the present invention are well suited for use in connection with enzymatic reaction systems, the same principles also apply to non-enzymatic reaction systems. Thus, in a further aspect, the present invention provides sensor for detecting an analyte in an environment including a first reaction system that is inhibited (that is, rendered unreactive or reduced in reactivity) by the presence of the analyte. The first reaction can, for example, include two compounds (or one or more compounds and a non-enzymatic catalyst) that react in the absence of the analyte, but the reaction thereof is limited or prevented by the presence of the analyte. For example, the analyte can be a poison for a catalyst present in the first reaction system. The sensor also includes at least a second reaction system that reacts to produce a first detectable state when the first reaction system is inhibited.

The present invention also provides a sensor for detecting an analyte in an environment including a first reaction system including a first compound that reacts with the analyte and at least a second reaction system that reacts to produce a first detectable state when the analyte is below a certain concentration.

In another aspect, the present invention provides a method of detecting an analyte in an environment including the steps of: providing a first reaction system that is inhibited by the presence of the analyte; and providing at least a second reaction system that reacts to produce a first detectable state when the first reaction system is inhibited.

In still another aspect, the present invention provides a method for detecting an analyte in an environment including the steps of: providing a first reaction system including a first compound, the analyte reacting with the first compound; and providing at least a second reaction system that reacts to produce a first detectable state when the analyte is below a certain concentration.

DETAILED DESCRIPTION OF THE INVENTION

Certain aspects of the present invention are discussed herein in the context of an enzymatic biosensor for the detection of nerve agents. In the detection of nerve agents, a biosensor with positive response signal is much more intuitive than a negative response sensor. A positive response sensor provides a changing signal in the presence of contamination. Table 1 compares the responses of existing biosensor technology with the present invention.

TABLE 1

Responses of existing biosensors and present invention

| Detection of | Existing technology | Present Invention |
| --- | --- | --- |
| Enzyme substrate | + | + |
| Lack of enzyme substrate | – | + |
| Enzyme Inhibitor | – | + |

The sensors and methods of the present invention address the shortcoming of negative response enzymatic biosensors. In, for example, the cases of inhibitor detection or the detection of compound/substrate deficiency, the present invention substantially improves previous sensors and methods by providing a positive signal even in the absence of an enzymatic reaction (Table 1).

Table 2 sets forth several non-exhaustive combinations of reaction products suitable to obtain an enzymatic positive response biosensor from a system that would otherwise provide only a negative response. Because of the wide range of, for example, hydrolase enzymes and colorimetric reactions, there are essentially unlimited possible combinations. The enzymes and colorimetric substrates can be soluble or immobilized. Immobilization of enzymes in polymeric media is disclosed, for example, in U.S. patent application Ser. No. 09/441,596, filed Nov. 17, 1999 and assigned to the assignee of the present invention, the disclosure of which is incorporated herein by reference. The enzyme(s) (of, for example, the first reaction system and/or the second reaction system) can, for example, be entrapped within a polymer medium of bonded to the polymer medium. Using pH-sensitive dyes, one can also combine an enzymatic hydrolysis reaction yielding either hydroxyl or hydronium ions (thereby changing pH) with a colorimetric reaction (that is, combination of rows 1 or 2 with row 3 of Table 2).

TABLE 2

Reaction products feasible to achieve
enzymatic positive response biosensor

| Reaction 1 (enzymatic sensing) | Reaction 2 (biocatalytic or chemical) | Signal |
|---|---|---|
| $H^+$ | $OH^-$ | pH change |
| $OH^-$ | $H^+$ | pH change |
| Color A | Color B | Color change |

In several embodiments, the present invention entails generally the incorporation of a second enzyme substrate pair or a second chemical reaction in addition to the sensing enzyme (or sensing substrate) for turning commonly negative response signals of enzyme biosensors into positive response signals. To characterize this invention, several representative reactions have been described suitable for incorporation in an existing enzymatic biosensor.

Figure 1:
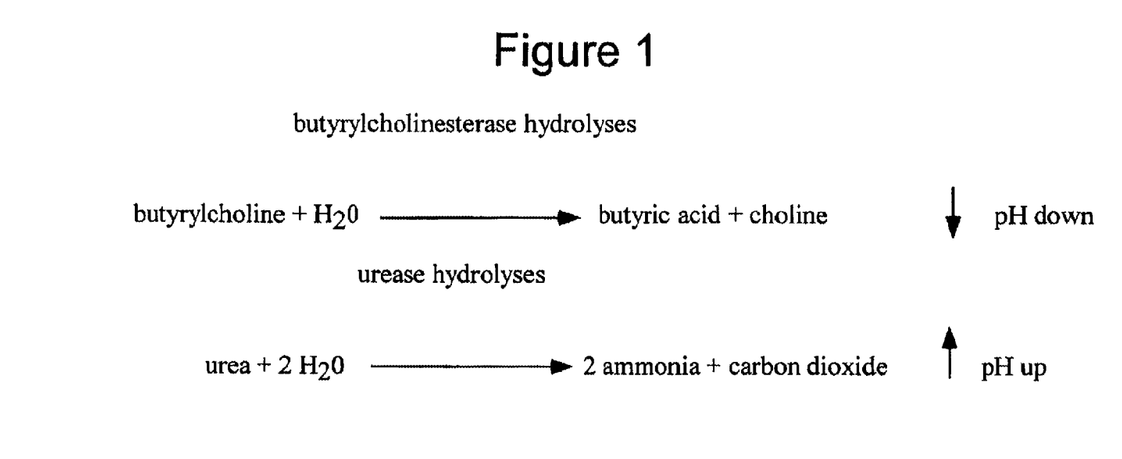
FIG. 1 illustrates reaction schematics of one embodiment of a sensor of the present invention for detecting nerve agents.
Figure 2:
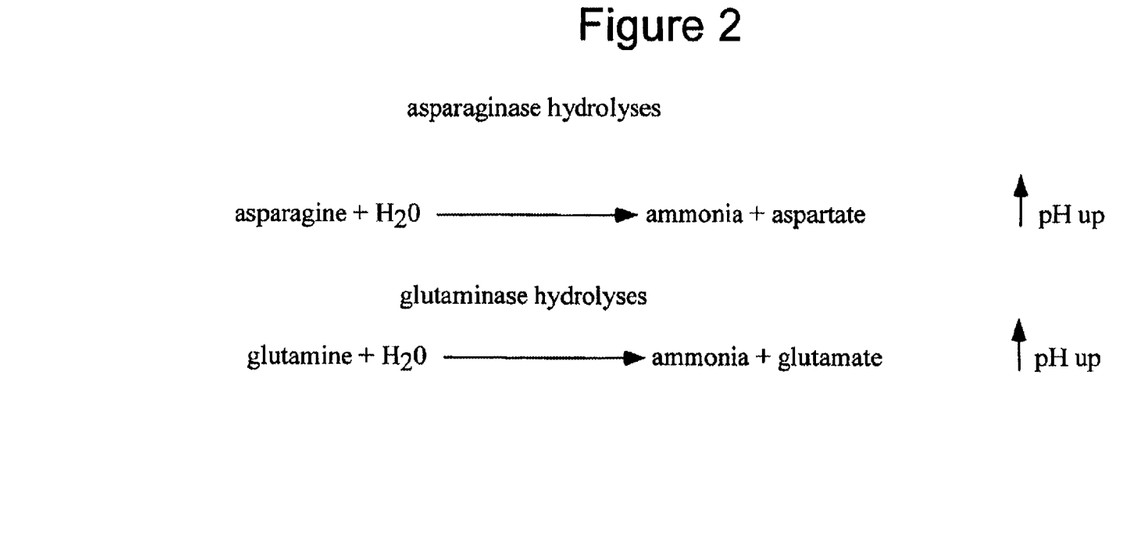
FIG. 2 illustrates additional reaction schematics suitable for production of basic conditions.

FIG. 1 illustrates reaction schematics of one embodiment of a sensor of the present invention for detecting nerve agents as discussed in further detail below. FIG. 2 illustrates additional examples of reaction schematics for production of base suitable for use in the enzymatic positive response biosensors of the present invention.

Figure 3:
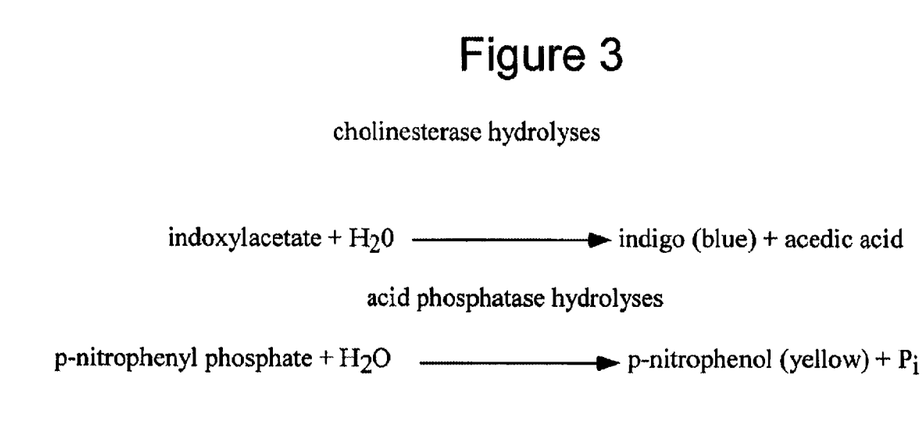
FIG. 3 illustrates examples of enzymatic reactions yielding colorimetric products.

FIG. 3 illustrates examples of enzymatic reactions yielding colorimetric products suitable for use in the enzymatic positive response biosensors of the present invention.

Figure 4:
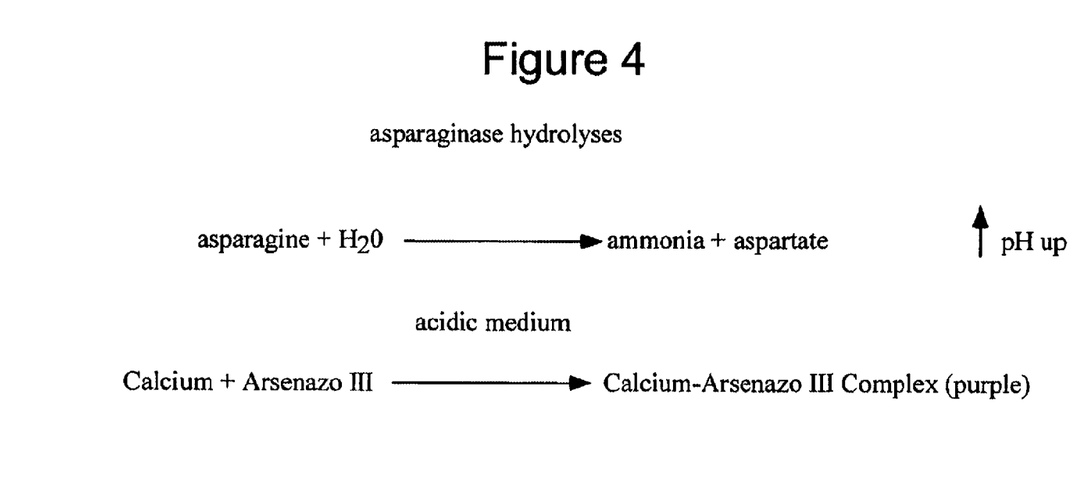
FIG. 4. illustrates an example of an enzymatic positive response biosensor incorporating an additional, non-enzymatic chemical reaction.

FIG. 4 illustrates enzymatic positive response biosensors of the present invention including a non-enzymatic additional chemical reaction. The sensing scheme of FIG. 4 can be used in detection of an asparaginase inhibitor. A similar approach is feasible with any other sensing enzyme yielding a basic product. The sensor yields a purple signal in the absence of enzymatic activity by the sensing enzyme (asparaginase, in this case).

To illustrate the present invention, enzymatic detection of diisopropyl fluorophosphate (DFP) by butyrylcholinesterase (BCHE) was studied. As a result of structural similarities, DFP can be viewed as an excellent model for nerve agents such as sarin and soman with less toxicity. Simonian, A. L., diSioudi, B. D., and Wild, J. R. *Analytica Chimica Acta*, 389, 189 (1999). A typical currently available sensor for detection of nerve agents includes cholinesterase paired with its respective substrate. When nerve agents are present, cholinesterase is inhibited and therefore signal development is retarded or nonexistent. Only in the absence of nerve agents does the enzymatically catalyzed reaction of the substrate occur. In the present invention, a second enzyme such as urease is added to a butyryl cholinesterase-based sensor. Hydroxide ions resulting from the formation of ammonium during hydrolysis of urea neutralize the protons produced during hydrolysis of cholinesterase substrate (butyrylcholine). When nerve agents are absent both enzymatic systems (see FIG. 1) are active and no pH change occurs. When an agent is present, hydroxide ions resulting from the hydrolysis of urea are not neutralized because butyryl cholinesterase is inhibited. The pH of the sensor then rises, resulting in a positive signal.

Figure 5:
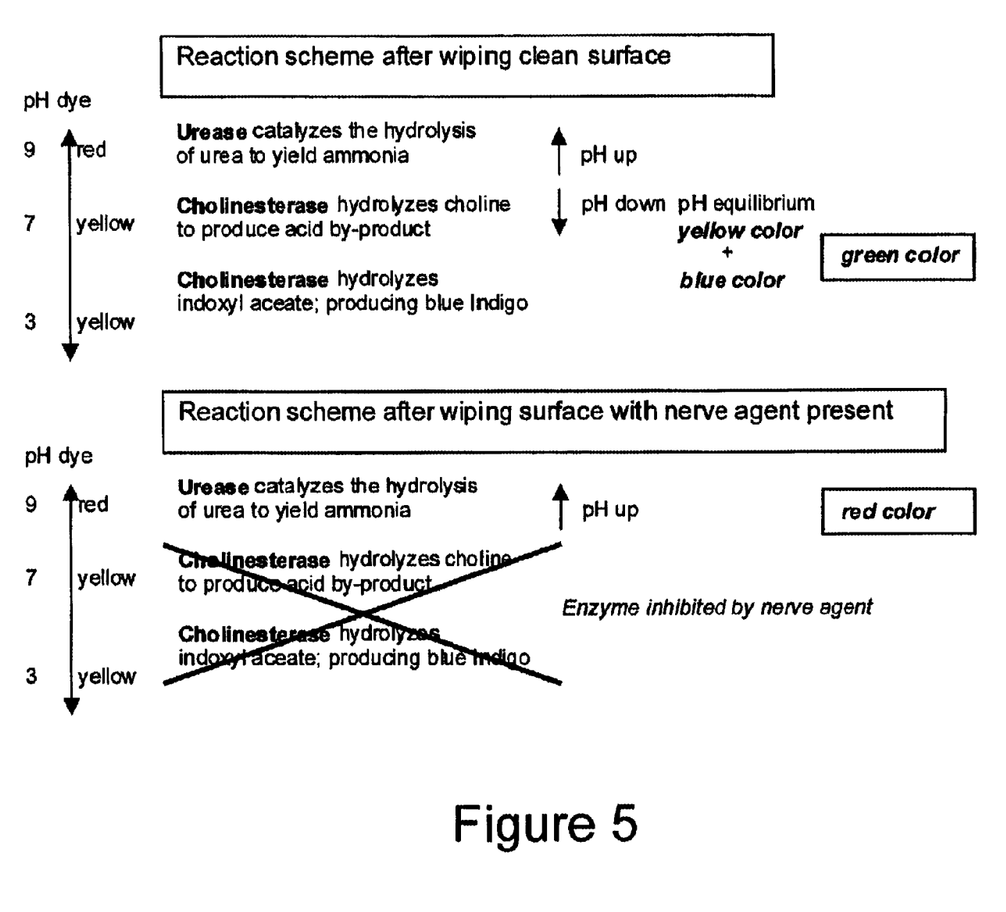
FIG. 5 illustrates reaction schematics of an example of detecting nerve agents with an additional reaction to produce a two-way color change

To improve the signal further it is possible to include an additional chromatic reaction to achieve a two-way color change. This two-way color change allows a positive response with two different colors in each of the case of the presence of nerve agent and absence of nerve agent. The reaction scheme illustrated in FIG. 5 sets forth such a two-way color change in the detection of nerve agents. In the case that nerve agents are present, the color changes from the original yellow to red as a result of inhibition of cholinesterase as described above. In the case of a clean surface (that is, the absence of nerve agents), however, the color changes from yellow to green as a result of the additional chromatic reaction, resulting in a self-explanatory signal for both the contaminated and clean surface.

The data of the studies of the present invention indicate that positive detection of small quantities of enzyme inhibitor is possible with the use of the novel sensors and methods of the present invention. The experimental studies also indicate that the reaction systems of the present invention can be utilized with sensors in either immobilized or soluble states.

Experimental Procedures

EXAMPLE 1

Figure 6:
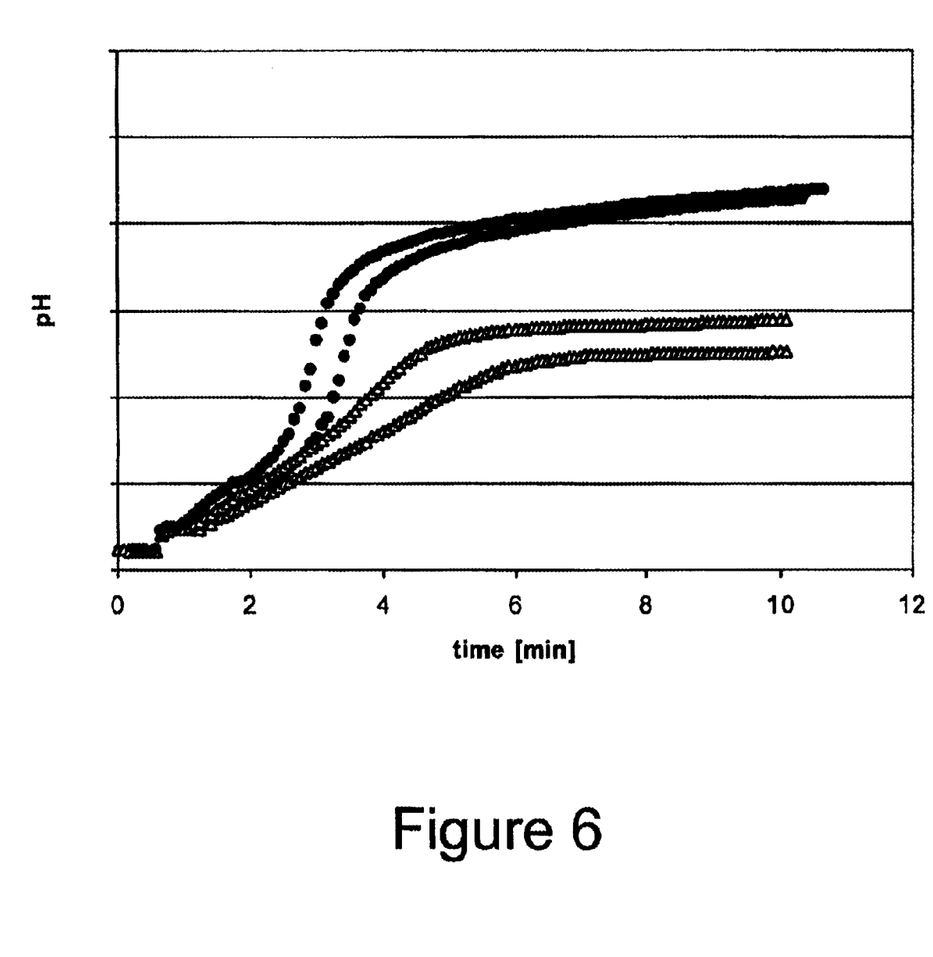
FIG. 6 illustrates studies of the detection of nerve agents in soluble systems (wherein solid circles represent studies with DFP present and empty triangles represent control studies with no agent present).

Utilizing a Positive Response Biosensor in Detection of DFP Using Soluble BChE and Urease In positive response enzymatic biosensors of the present invention including soluble BChE (0.14 mg per mL substrate solution) and urease (0.02 mg per mL substrate solution), hydroxide ions resulting from urea hydrolysis (50 mM) neutralize protons produced during butyrylcholine hydrolysis (100 mM). The pH stabilizes at a value of approximately 6.6 in the absence of DFP. resulting in no signal change (see FIG. 6.). When DFP is present, hydroxide ions resulting from urea hydrolysis are not neutralized and the pH increases; triggering a positive signal.

EXAMPLE 2

Preparation and Sensing Application of Biocatalytic Polymers

BCHE from horse serum and urease from Jack Beans were polymerized using a method similar to that described previously in LeJeune, K. E., Mesiano, A. J., Bower, S. B., Grimsley, J. K., Wild, J. R., and Russell, A. J. *Biotechnol. Bioeng.* 54, 105 (1997). LeJeune, K. E., and Russell, A. J. *Biotechnol. Bioeng.* 51, 450 (1996), the disclosures of which are incorporated herein by reference. Hypol 3000 polyurethane prepolymer (4 g) and enzyme-buffer solution (4 mL) were agitated for 20 seconds with an oar-shaped mixer head at 2500 rpm. The aqueous phase contained 10 mM Tris buffer (pH 8.0), 1% (w/w) F68 surfactant, 0.2% (w/w) cresol red—pH dye and enzymes. The polymerization was complete in a few minutes and the biopolymer could be utilized in sensing applications after a 24 h drying period.

Glass surfaces (70 cm$^2$) were contaminated with DFP (10 mg/m$^2$). Control experiments were conducted with clean surfaces. A butyrylcholine and urea solution (1 mL of 100 mM and 50 mM respectively) was then added to biopolymer sponge disks 100 and 100a (see FIG. 7) before using them to uniformly wipe polymer disks 100 and 100a.

Figure 7:
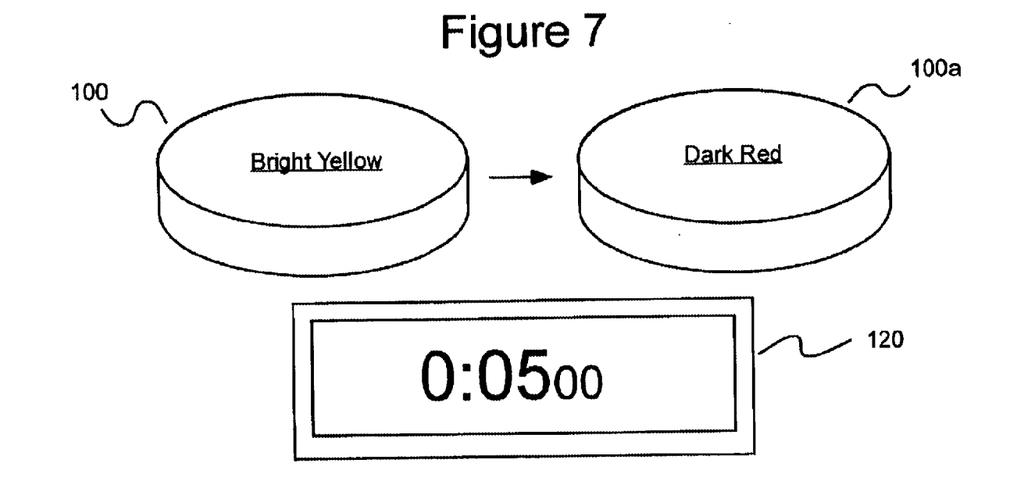
FIG. 7 illustrates the color state of cresol red, urease and butyrylcholinesterase containing polyurethane copolymers 5 minutes after wiping control and contaminated surfaces.

Within 2 minutes after wiping the contaminated surfaces a color change from yellow to red was observed in polymer disk 100a, whereas polymer disk 100 remained yellow after wiping the clean (that is, uncontaminated with DFP) control surfaces. The signal represents a positive response with no color change after wiping the clean surface and positive signal in form of red color after wiping the contaminated surface. FIG. 7 illustrates the sensor signal 5 minutes after application as determined by counter 120. Existing cholinesterase sensing technology would indicate a color change only after wiping the clean surface. The negative response of existing sensors indicates full enzymatic activity and no inhibition.

EXAMPLE 3

Color-Dependence of pH Sensitive Dye Containing Polymers

Figure 8:
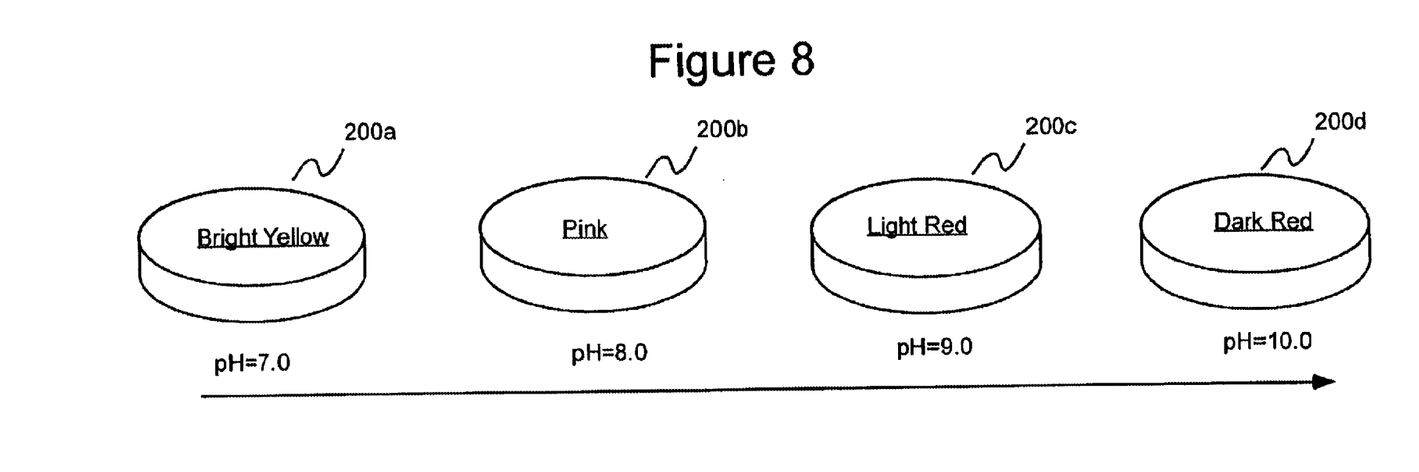
FIG. 8 illustrates the pH-dependent color of cresol red dye-containing polymers.

Utilizing the aforementioned procedures for polymer synthesis, cresol red dye-containing polymer sponge disks 200a–200d were synthesized having a dye content of 2 mg dye/g dry polymer. FIG. 8 illustrates the effective physical property differences incurred when polymer disks 200a–200d were incubated within aqueous solutions of varying pH. Sample colors ranged from bright yellow at pH 7.0 to red at pH 10.0.

EXAMPLE 4

Figure 9:
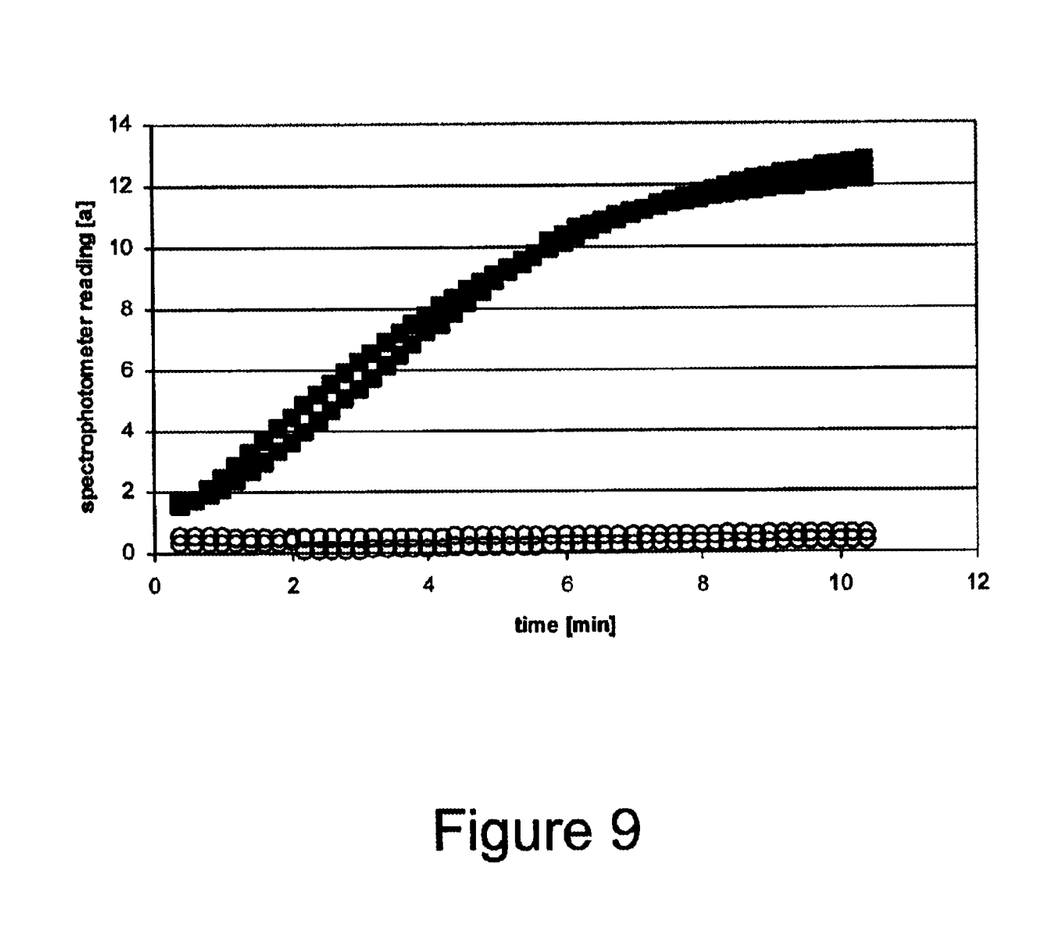
FIG. 9 illustrates numerical data from a solid spectrophotometer analytical device after surface application of a positive response biosensor of the present invention (wherein squares represent studies with $1.0\,\mu g/cm^2$ DFP and circles represent control studies with no DFP present).

Utilizing the Positive Response Biosensor in Detection of DFP Using BChE and Urease Immobolized in Polyurethane The positive response enzymatic biosensor with immobilized BCHE, urease and a pH-sensitive dye (cresol red), operated generally under the same principle as described above. Hydroxide ions resulting from the formation of ammonia neutralized any protons produced during hydrolysis of butyrylcholine. No color change from the original yellow was observed as a result of stabilized pH when both enzymes are active. In the presence of DFP, however, BChE is significantly inhibited while urease remains active. Only hydroxide ions are produced and the pH increases accordingly. Increasing pH results in a color change of incorporated dye and the sensor changes from yellow to red. The color change is easily recognized by the naked eye. To remove any subjectivity from the experimental procedures, however, a solid-phase Minolta CM-500d solid spectrophotometer was used to monitor the sensor's color change. This unit uses a three-dimensional color coordinate system (L*a*b) to define colors and intensity. The biopolymer containing cresol red develops a yellow color when pH is below 7.0 and turns to red at a pH around 8.8. Each kinetic reaction was performed in duplicate (see FIG. 9). It is clear that a positive response was observed in the presence of DFP, a powerful inhibitor of the cholinesterase sensing enzyme used in this sensor construct.

Although the present invention has been described in detail in connection with the above examples, it is to be understood that such detail is solely for that purpose and that variations can be made by those skilled in the art without departing from the spirit of the invention except as it may be limited by the following claims.

What is claimed is:

1. A sensor for detecting an analyte in an environment, the sensor comprising:
   a first reaction system including a first enzyme and a substrate for the first enzyme, the analyte inhibiting the first enzyme; and
   at least a second reaction system that reacts to produce a first detectable state only when the first enzyme is inhibited.

2. The sensor of claim 1 wherein the reaction of the first reaction system produces a second detectible state, different from the first detectible state.

3. The sensor of claim 1 wherein the reaction of the first reaction system causes pH to change in a first direction and the reaction of the second reaction system causes pH to change in a second direction, opposite of the first direction.

4. The sensor of claim 3 wherein the first enzyme is a hydrolase.

5. The sensor of claim 3 wherein the second reaction system comprises a second enzyme and a substrate for the second enzyme.

6. The sensor of claim 5 wherein the first enzyme is a hydrolase and the second enzyme is a different hydrolase.

7. The sensor of claim 3 wherein the first detectible is a colorimetric change.

8. The sensor of claim 3 wherein the reaction of the first reaction system produces a second detectible state, different from the first detectible state.

9. The sensor of claim 8 wherein the first detectible state arises from the presence of a first pH sensitive dye producing a colorimetric change and the second detectible state is a colorimetric change different from the colorimetric change of the first detectible state.

10. The sensor of claim 3 wherein the first enzyme is a cholinesterase.

11. The sensor of claim 10 wherein the analyte is a nerve agent.

12. The sensor of claim 1 wherein the reaction of the first reaction system causes a first colorimetric change and the reaction of the second reaction system causes a second colorimetric change, the second colorimetric change being different from the first colorimetric change.

13. The sensor of claim 12 wherein the first enzyme is a hydrolase.

14. The sensor of claim 12 wherein the second reaction system includes a second enzyme and a substrate for the second enzyme.

15. The sensor of claim 14 wherein the first enzyme is a hydrolase and the second enzyme is a different hydrolase.

16. The sensor of claim 12 wherein the first enzyme is a cholinesterase.

17. The sensor of claim 16 wherein the analyte is a nerve agent.

18. The sensor of claim 1 wherein the reaction of the first reaction system causes pH to change in a first direction and the reaction of the second reaction system causes a pH sensitive colorimetric change when the first enzyme is inhibited.

19. The sensor of claim 18 wherein the first enzyme is a hydrolase.

20. The sensor of claim 18 wherein the second reaction system includes a second enzyme and a substrate for the second enzyme.

21. The sensor of claim 20 wherein the first enzyme is a hydrolase and the second enzyme is a different hydrolase.

22. The sensor of claim 18 wherein the first enzyme is a cholinesterase.

23. The sensor of claim 22 wherein the analyte is a nerve agent.

24. The sensor of claim 1 wherein the first enzyme is immobilized in a polymer medium.

25. The sensor of claim 1 wherein the first enzyme is immobilized in a polymer medium, the second reaction system includes a second enzyme and the second enzyme is immobilized in the polymer medium.

26. A sensor for detecting an analyte in an environment, the sensor comprising:
   a first reaction system including a first enzyme or a first substrate, the analyte being a substrate for the first enzyme if the first reaction system includes the first enzyme or the first enzyme if the first reaction system includes the first substrate; and at least a second reaction system that reacts to produce a first detectable state only when the analyte is below a certain concentration.

27. The sensor of claim 26 wherein the reaction of the analyte catalyzed by the first enzyme produces a second detectible state, different from the first detectible state.

28. The sensor of claim 26 wherein the reaction of the analyte catalyzed by the first enzyme causes pH to change in a first direction and the reaction of the second reaction system causes pH to change in a second direction, opposite of the first direction.

29. The sensor of claim 28 wherein the first enzyme is a hydrolase.

30. The sensor of claim 28 wherein the second reaction system comprises a second enzyme and a substrate for the second enzyme.

31. The sensor of claim 30 wherein the first enzyme is a hydrolase and the second enzyme is a different hydrolase.

32. The sensor of claim 28 wherein the first detectible state is a colorimetric change.

33. The sensor of claim 28 wherein the reaction of the analyte catalyzed by the first enzyme produces a second detectible state, different from the first detectible state.

34. The sensor of claim 33 wherein the first detectible state arises from the presence of a first pH sensitive dye producing a colorimetric change and the second detectible state is a colorimetric change different from the colorimetric change of the first detectible state.

35. The sensor of claim 26 wherein the reaction of the analyte catalyzed by the first enzyme causes a first colorimetric change and the reaction of the second reaction system causes a second colorimetric change, the second colorimetric change being different from the first colorimetric change.

36. The sensor of claim 35 wherein the first enzyme is a hydrolase.

37. The sensor of claim 35 wherein the second reaction system includes a second enzyme and a substrate for the second enzyme.

38. The sensor of claim 37 wherein the first enzyme is a hydrolase and the second enzyme is a different hydrolase.

39. The sensor of claim 26 wherein the reaction of the first reaction system causes pH to change in a first direction and the reaction of the second reaction system causes a pH sensitive colorimetric change when the analyte is below a certain concentration.

40. The sensor of claim 39 wherein the first enzyme is a hydrolase.

41. The sensor of claim 39 wherein the second reaction system includes a second enzyme and a substrate for the second enzyme.

42. The sensor of claim 41 wherein the first enzyme is a hydrolase and the second enzyme is a different hydrolase.

43. The sensor of claim 26 wherein the first enzyme is immobilized in a polymer medium.

44. The sensor of claim 26 wherein the first enzyme is immobilized in a polymer medium, the second reaction system includes a second enzyme and the second enzyme is immobilized in the polymer medium.

45. A method of detecting an analyte in an environment, the method comprising the steps of:

providing a first reaction system including a first enzyme and a substrate for the first enzyme, the analyte inhibiting the first enzyme; and providing at least a second reaction system that reacts to produce a first detectable state only when the first enzyme is inhibited.

46. The method of claim 45 wherein the reaction of the first reaction system produces a second detectible state, different from the first detectible state.

47. A method for detecting an analyte in an environment, the method comprising the steps of:

providing a first reaction system including a first enzyme or a first substrate for the first enzyme, the analyte being a substrate for the first enzyme if the first reaction system includes the first enzyme or the first enzyme if the first reaction system includes the first substrate for the first enzyme; and providing at least a second reaction system that reacts to produce a first detectable state when only the analyte is below a certain concentration.

48. The method of claim 47 wherein the reaction of the first reaction system produces a second detectible state, different from the first detectible state.

49. A sensor for detecting an analyte in an environment, the sensor comprising:

a first reaction system that is reduced in reactivity by the presence of the analyte; and at least a second reaction system that reacts to produce a first detectable state only when the first reaction system is inhibited.

50. A sensor for detecting an analyte in an environment, the sensor comprising:

a first reaction system including a first compound that produces a reaction with the analyte; and at least a second reaction system that reacts to produce a first detectable state only when the analyte is below a certain concentration.

51. A method of detecting an analyte in an environment, the method comprising the steps of:

providing a first reaction system that is reduced in reactivity by the presence of the analyte; and providing at least a second reaction system that reacts to produce a first detectable state only when the first reaction system is inhibited.

52. The method of claim 51 wherein the reaction of the first reaction system produces a second detectible state, different from the first detectible state.

53. A method for detecting an analyte in an environment, the method comprising the steps of:

providing a first reaction system including a first compound, the first compound causing a reaction with the analyte; and providing at least a second reaction system that reacts to produce a first detectable state only when the analyte is below a certain concentration.

54. The method of claim 53 wherein the reaction of the analyte with the first compound produces a second detectible state, different from the first detectible state.

* * * * *

UNITED STATES PATENT AND TRADEMARK OFFICE
CERTIFICATE OF CORRECTION

PATENT NO.   : 6,750,033 B2
DATED        : June 15, 2004
INVENTOR(S)  : Keith E. Lejeune and Markus Erbeldinger It is certified that error appears in the above-identified patent and that said Letters Patent is hereby corrected as shown below:

<u>Column 1,</u>
Line 3, after the title and before "BACKGROUND OF THE INVENTION" add the following text:

-- GOVERNMENT INTEREST

This invention was made with Government support under Contract No. DAAD19-01-C-0043 awarded by the Department of Defense. The Government has certain rights in the invention. --

Signed and Sealed this

Seventh Day of September, 2004

JON W. DUDAS
*Director of the United States Patent and Trademark Office*